United States Patent [19]

Schneider

[11] 4,165,438
[45] Aug. 21, 1979

[54] SYNTHESIS OF ACRYLIC ACIDS AND ESTERS

[75] Inventor: Ronald A. Schneider, Albany, Calif.

[73] Assignee: Chevron Research Company, San Francisco, Calif.

[21] Appl. No.: 734,065

[22] Filed: Oct. 20, 1976

Related U.S. Application Data

[63] Continuation-in-part of Ser. No. 356,887, May 3, 1973.

[51] Int. Cl.$^2$ .............................................. C07C 69/54
[52] U.S. Cl. ..................................... 560/211; 562/599
[58] Field of Search ........................ 260/486; 560/211; 562/599

[56] References Cited

FOREIGN PATENT DOCUMENTS 1294956  5/1969  Fed. Rep. of Germany ...... 260/486 D

Primary Examiner—Paul J. Killos
Attorney, Agent, or Firm—D. A. Newell; John Stoner, Jr.; A. T. Bertolli

[57] ABSTRACT

Acrylic acids and esters are produced by reacting a lower alkanoic acid or lower alkyl ester thereof with formaldehyde in the presence of a vanadium orthophosphate catalyst having an intrinsic surface area of from about 10 m$^2$/g to about 50 m$^2$/g.

5 Claims, No Drawings

SYNTHESIS OF ACRYLIC ACIDS AND ESTERS

CROSS-REFERENCE TO RELATED APPLICATION

This application is a continuation-in-part of copending application Ser. No. 356,887, filed May 3, 1973.

DESCRIPTION OF THE PRIOR ART

German Patent No. 1,294,956 of Farbwerke Hoechst AG, discloses the preparation of methyl acrylate by oxidation of methyl acetate and subsequent condensation of formaldehyde with methyl acetate in a single stage using a catalyst consisting of 15–40 weight percent titanium dioxide, 20–40 weight percent vanadium pentoxide, and 20–65 weight percent phosphoric acid.

Japanese Patent No. 71/16728 of Toa Gosei Chemical Industry Co., Ltd., discloses the preparation of acrylic acids, e.g., acrylic acid, methacrylic acid, or the methyl ester thereof, by reacting acetic acid, propionic acid or the methyl ester thereof with formaldehyde in the presence of alkali and alkaline earth metal metaphosphates.

U.S. Pat. No. 3,014,958 of Koch et al discloses preparation of acrylic esters by reacting alkanoic acid esters and formaldehyde in the presence of alkali and alkaline earth metal phosphates, and aluminum phosphate.

SUMMARY OF THE INVENTION

It has now been found that lower acrylic acids and esters are produced in high selectivity and yields by reacting a lower alkanoic acid or lower alkyl ester thereof with formaldehyde in the presence of a vanadium orthophosphate catalyst which has an intrinsic surface area of from about 10 m$^2$/g to about 50 m$^2$/g. Particularly good results are obtained with a vanadium orthophosphate catalyst having a P/V atomic ratio of 1:1 to 1.5:1 and an average vanadium valence of about 4.1 to 4.4.

DESCRIPTION OF THE INVENTION

The process of the invention may be represented by the following net reaction (1)

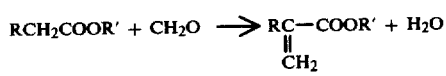

$$RCH_2COOR' + CH_2O \longrightarrow RC{-}COOR' + H_2O \quad (1)$$
$$\phantom{RCH_2COOR' + CH_2O \longrightarrow R}\|$$
$$\phantom{RCH_2COOR' + CH_2O \longrightarrow R}CH_2$$

wherein R is a lower alkyl group, e.g., methyl, ethyl, propyl or butyl, and R' is hydrogen or R.

Illustrative lower alkanoic acid reactants represented by RCH$_2$COOR' are acetic acid, propionic acid and butyric acid. Illustrative lower alkyl alkanoate reactants represented by RCH$_2$COOR' are methyl acetate, methyl propionate and ethyl butyrate. The preferred alkanoic acid reactants are acetic and propionic acid, and the preferred alkyl alkanoate reactants are methyl acetate and methyl propionate.

Examples of acrylic acids and esters produced by the process of the invention are acrylic acid, methacrylic acid, methyl acrylate and methyl methacrylate.

Any of the various types of formaldehyde-containing materials can be used in the process of the invention; for example, paraformaldehyde, trioxane, aqueous solutions of formaldehyde and alcoholic solutions of formaldehyde. However, an aqueous formaldehyde solution, e.g., a 30–32 weight percent solution, is preferred in the practice of the process. The molar ratio of alkanoic acid or alkyl alkanoate reactant to formaldehyde can be varied within a range of about 1:1 to 20:1. Generally, alkanoic acid or alkyl alkanoate to formaldehyde molar ratios from about 5:1 to 15:1 are preferred.

While limited amounts of water or alcohol may be present in the reaction mixture from the aqueous or alcoholic formaldehyde solutions used in the process of the invention, there is ordinarily no major advantage in conducting the process of the reaction in the presence of solvents. When water or alcohol is present, the molar ratio of water or alcohol to formaldehyde is generally about 5:1 to 1:5.

The reaction depicted in reaction (1) is performed in the presence of a vanadium orthophosphate catalyst. The vanadium orthophosphates suitably employed are characterized by an intrinsic surface area of about 10 to 50 m$^2$/g, preferably about 20 to 50 m$^2$/g; a phosphorus-to-vanadium atomic ratio in the range of from 0.9:1 to 1.8:1, preferably 1:1 to 1.5:1, a vanadium valency of about 3.9 to 4.6, preferably 4.1 to 4.4; and a phosphorus valency of about 5. The vanadium phosphate can be employed in granular particulate form or in fluidized bed form, and can be used in conjunction with suitable supports.

Vanadium orthophosphates prepared by conventional methods are generally suitable for the process of the invention. However, the preferred vanadium orthophosphate catalysts having a high surface area, e.g., 10 to 50 m$^2$/g, are prepared by precipitation from an essentially organic medium. The preparation is generally conducted by reacting a solution of a vanadium compound, e.g., an oxide, halide or oxychloride compound, with phosphoric acid in an organic solvent, e.g., oxygenated organic solvents such as alkanols, ethers and ketones, at a temperature of about 20° to 150° C., and subsequently precipitating the resulting vanadium orthophosphate by evaporation of the organic solvent. The vanadium orthophosphate catalysts prepared by precipitation from an organic solvent generally exhibit the characteristics of long catalyst life and excellent retention of selectivity.

In practice, the vanadium orthophosphate catalyst is generally subjected to pretreatment or activation prior to use in the process of the invention. In general, the activation comprises heating the catalyst in an atmosphere of an oxygen-containing gas, e.g., air. Activation temperatures from about 350° C. to 750° C. are satisfactory. Typical activation times are from about 1 hour to 18 hours.

The process of the invention is conducted in the vapor phase with continuous or batch process techniques. In the preferred modification, the feed mixture is vaporized and, while in the vapor phase, passed over the catalyst maintained in a continuous reactor at reaction temperature and pressure. The reaction mixture is recovered and condensed, and the acrylic acid or ester product is recovered by distillation. It is also desirable to recover and reuse unreacted starting materials. Vanadium catalysts which become deactivated during use can be reactivated by heating in a manner similar to that hereinbefore described for initial activation of the catalysts.

The process of the invention is satisfactorily performed at a temperature from 300° to 500° C., although a temperature from 350° to 425° C. is preferred. The process is normally conducted at atmospheric pressure, although higher or lower pressures may be used.

The space velocity of the feed mixture passed over the catalyst when operating in a continuous manner can be varied over wide limits. In this specification, the feed mixture space velocity over the catalyst is expressed as total volume of gaseous feed mixture per unit time per unit volume of catalyst, corrected to 0° C. and 1 atmosphere pressure. A useful space velocity range includes from about 100 liters of gaseous feed mixture per hour per liter of catalyst to about 6000 liters of gaseous feed mixture per hour per liter of catalyst.

EXAMPLES

EXAMPLE 1

Comminuted vanadium pentoxide ($V_2O_5$) and isobutanol were charged to a glass-lined reactor fitted for stirring, temperature control, the introduction of an inert gas into the isobutanol and for the exclusion of water vapor. For each formula weight in grams of the vanadium pentoxide, about 1 liter of the isobutanol solvent was used. The resulting slurry was then stirred and the vanadium pentoxide was dissolved in the isobutanol by passing a stream of anhydrous hydrogen chloride gas into the slurry while maintaining the temperature between 30° and 40° C. After the resulting solution became red-brown colored and nearly saturated with hydrogen chloride gas, it was ready for mixing with a solution of orthophosphoric acid ($H_3PO_4$) in isobutanol.

The orthophosphoric acid solution was prepared by adding crystalline, 100% orthophosphoric acid to isobutanol in a glass-lined vessel large enough to accommodate the solution of vanadium oxide prepared as described above and the phosphoric acid solution. For each mol of the acid, a volume of about 100 ml of isobutanol was used. Sufficient orthophosphoric acid was charged to the vessel to yield, upon the addition of the red-brown solution of dissolved vanadium oxide, a phosphorus-to-vanadium atomic ratio of 0.9. The vessel was fitted for stirring, temperature control, reflux, the introduction of the red-brown solution, and for the exclusion of water vapor.

After the introduction of the red-brown solution to the phosphoric acid solution in the second vessel, the temperature of the resulting solution was increased to the reflux temperature, i.e., about 110° C., and maintained for about 1.5 hours. The solution changed to a greenish-brown color. Thereafter, the reflux condenser was removed and isobutanol solvent was distilled from the reaction mixture. During the above heating at reflux and subsequently during distillation, hydrogen chloride gas evolved from the solution and was vented.

As the heating continued and the volatiles, mainly isobutanol and hydrogen chloride, were evolved, the color of the solution continued to change; transitorily it assumed various shades of green or blue, the colorations associated with vanadium in the +4 valence (oxidation) state. Finally, after about two-thirds of the solvent was evolved, the solution was colored a greenish-blue. Some light-blue precipitate was present in the concentrate at this time. The remainder of the volatiles was conveniently removed by placing the concentrate in a loosely covered glass vessel in a ventilated oven maintained at 150° C. Drying was continued until the resulting precipitated solid reached a substantially constant weight.

The dried precipitate was a uniform, very dark, green-gray solid which after activation had a surface area of about 23 $m^2/g$ as measured by the method of Brunauer, Emmett and Teller (BET) described in the J. Amer. Chem. Soc. 60, 309 (1938). It was broken up and sieved to a 20–28 mesh (Tyler Screen) size.

EXAMPLE 2

A vanadium orthophosphate catalyst having a P/V atomic ratio of 1.2 and a surface area of 16 $m^2/g$ (BET) was prepared by the procedure of Example 1.

EXAMPLE 3

A vanadium orthophosphate catalyst having a P/V atomic ratio of 1.8 and surface area of 12 $m^2/g$ (BET) was prepared by the procedure of Example 1.

EXAMPLE 4

A vanadium orthophosphate catalyst was prepared by the following procedure.

A solution of vanadium oxychloride ($VOCl_3$) and 100% phosphoric acid in tetrahydrofuran (THF) was prepared. The mol ratio of $VOCl_3$ to $H_3PO_4$ was 1:1.2 and the amount of THF was 500 ml per gram-atom of phosphorus. The solution was heated to evaporate the THF. Heating was continued until the resulting residue of vanadium orthophosphate reached a substantially constant weight. The vanadium orthophosphate product was broken up and sieved to 20–28 mesh (Tyler Screen) size. The surface area of the product was 22 $m^2/g$ (BET).

EXAMPLE 5

A 45.5-g sample of vanadium pentoxide was ground to a very fine powder. To the vanadium pentoxide was added 57.6 g of 85% phosphoric acid with vigorous stirring. The resulting mixture set to a nearly solid mass in less than 10 minutes. The mixture was then dried at 150° C. overnight. The vanadium orthophosphate product was crushed and sieved to 14–28 mesh (Tyler Screen) size. The P/V atomic ratio was 1.0 and the surface area was 3 $m^2/g$ (BET).

EXAMPLE 6

A mixture of vanadium pentoxide and 37% hydrochloric acid (16 ml hydrochloric acid per gram vanadium pentoxide) was heated under reflux for about 20 hours. Phosphoric acid (85 weight percent) was then added to the resulting vanadium oxydichloride solution in an amount sufficient to yield a P/V atomic ratio of 1.2. The solution was then concentrated by evaporating water at a bath temperature of 150° C. until a thick slurry was produced. The slurry was then placed in an oven maintained at 150° C. and heated overnight. The resulting vanadium orthophosphate product was crushed and sieved to 20–28 mesh (Tyler Screen) size. The surface area of the product was 3 $m^2/g$ (BET).

The vanadium orthophosphate catalysts prepared in Examples 1–6 were employed for the preparation of acrylic acid from acetic acid and formaldehyde by the following procedure. Each was activated prior to use by heating in air for several hours.

Approximately 10–20 cc of the catalyst was placed in a ½-inch-diameter reactor tube. The reactor tube was heated to reaction temperature. A reaction mixture of acetic acid, formaldehyde and water in a molar ratio of 10:1:2.8 was then vaporized and passed through the reactor at a volume hourly space velocity of 400 $hr^{-1}$. The product mixture collected during the first 20 minutes of operation was analyzed by gas chromatographic and nuclear magnetic resonance techniques.

The catalyst employed, the P/V atomic ratio, the reaction temperature, the conversion of formaldehyde, the selectivity to acrylic acid and the yield of acrylic acid based on converted formaldehyde are tabulated in Table I.

TABLE I

| Run No. | Catalyst | Surface Area, m²/g | P/Metal Ratio | Temp., °C. | Formaldehyde Conversion, % | Acrylic Acid Selectivity, mol % | Yield, mol % |
|---|---|---|---|---|---|---|---|
| 1 | Example 1 | 23 | 0.9 | 360 | 42 | 88 | 33 |
| 2 | Example 2 | 16 | 1.2 | 360 | 98 | 86 | 73 |
| 3 | Example 3 | 12 | 1.8 | 360 | 59 | 100 | 60 |
| 4 | Example 4 | 22 | 1.2 | 360 | 85 | 86 | 73 |
| 5 | Example 5 | 3 | 1.0 | 375 | 73 | 100 | 73 |
| 6 | Example 6 | 3 | 1.2 | 360 | 54 | 100 | 54 |

All six catalysts showed high selectivity and good yields for the first 20 minutes. However, as time went on, catalysts with surface areas exceeding 10 m²/g exhibited surprisingly longer catalyst life and better retention of selectivity than those of surface area less than 10 m²/g. For example, after approximately 140 minutes onstream, the instantaneous yield of acrylic acid was about 63 mol percent with the high-surface-area catalyst of Run 4. However, after approximately 70 minutes onstream, the instantaneous yield of acrylic acid was only about 28 mol percent with the low-surface-area catalyst of Run 5.

EXAMPLES 7-19

For comparison purposes, a variety of metal phosphate compounds were tested as catalysts for the preparation of acrylic acid from acetic acid, formaldehyde and water by a procedure similar to that used for the vanadium orthophosphate catalysts of Runs 1-6. The metal phosphates tested and the results are tabulated in Table II.

TABLE II

| Run No. | Catalyst | Temp., °C. | Formaldehyde Conversion, % | Acrylic Acid Selectivity, mol % | Yield, mol % |
|---|---|---|---|---|---|
| 7 | Lithium orthophosphate | 400 | 38 | 56 | 21 |
| 8 | Lithium orthophosphate | 425 | 33 | 60 | 20 |
| 9 | Lithium metaphosphate | 375-475 | <1 | — | — |
| 10 | Lithium pyrophosphate | 375-475 | <1 | — | — |
| 11 | Sodium tripolyphosphate | 450 | 12-15 | 40-50 | 6 |
| 12 | Magnesium orthophosphate | 425 | 31-35 | 65-70 | 23 |
| 13 | Zinc orthophosphate | 400 | 32 | 50 | 16 |
| 14 | Aluminum orthophosphate | 425 | — | — | 4 |
| 15 | Chromium orthophosphate | 400 | 14 | 85 | 12 |
| 16 | Cerium orthophosphate | 425 | — | — | 18 |
| 17 | Niobium orthophosphate | 375 | 30 | 80 | 24 |
| 18 | Antimony orthophosphate | 425 | 28 | 65 | 18 |
| 19 | Bismuth orthophosphate | 395 | 52 | 88 | 46 |

I claim:

1. A process for producing acrylic acid and esters which comprises passing into a reaction zone the reactants formaldehyde and a lower alkanoic acid or lower alkyl ester thereof and therein reacting said reactants in the vapor phase at a temperature of about 300° C. to 500° C. in the presence of a catalyst consisting essentially of vanadium orthophosphate having an intrinsic surface area of from about 10 to about 50 m²/g and a P/V atomic ratio of 1:1 to 1.5:1.

2. The process of claim 1 wherein the molar ratio of alkanoic acid or ester thereof to formaldehyde is 5:1 to 15:1.

3. The process of claim 2 wherein the reaction is conducted in the presence of water as a diluent.

4. The process of claim 3 wherein the alkanoic acid is acetic acid.

5. The process of claim 3 wherein the alkanoic acid is propionic acid.

* * * * *